United States Patent [19]

Schomburg

[11] Patent Number: 4,467,813
[45] Date of Patent: Aug. 28, 1984

[54] BIOLOGICAL SIGNAL SOURCE AMPLIFIER

[75] Inventor: Richard A. Schomburg, Hillsboro, Oreg.

[73] Assignee: Cardiac Resuscitator Corporation, Wilsonville, Oreg.

[21] Appl. No.: 374,697

[22] Filed: May 4, 1982

[51] Int. Cl.³ ............................................... A61B 5/04
[52] U.S. Cl. ...................................... 128/702; 128/902
[58] Field of Search .................................. 128/696–706, 128/419 P, 419 PG, 419 D, 902

[56] References Cited

U.S. PATENT DOCUMENTS

| Re. 30,750 | 9/1981 | Diack et al. | 128/419 PG |
| 3,476,103 | 11/1969 | Stenger | 128/902 |
| 3,533,003 | 10/1970 | Plascynski | 128/902 |
| 3,656,487 | 2/1973 | Welborn | 128/419 PG |
| 3,716,059 | 12/1975 | Gobeli | 128/419 PG |
| 3,927,677 | 4/1976 | Brownlee et al. | 128/419 PG |
| 3,972,334 | 8/1976 | Rockland | 128/419 PG |
| 4,114,627 | 9/1978 | Lewyn et al. | 128/419 PG |
| 4,184,493 | 1/1980 | Langer et al. | 128/419 D |
| 4,202,340 | 5/1980 | Langer et al. | 128/419 D |
| 4,261,365 | 4/1981 | Nordling | 128/419 PG |
| 4,300,566 | 11/1981 | Stindt | 128/419 PG |

Primary Examiner—William E. Kamm
Assistant Examiner—Foley Deidre A.
Attorney, Agent, or Firm—Chernoff, Vilhauer, McClung, Birdwell & Stenzel

[57] ABSTRACT

A biological signal source amplifier having a rapid overload recovery capability and an output reference level translation feature. The amplifier responds to input signals of excessive amplitude by actively decreasing the response time of a reactive input coupling circuit when the input signal crosses predetermined dynamic limits. A differential amplifier is used in such a way as to produce an output referenced to a voltage level other than power supply ground. A level translation feature is provided for translating the output signal to the input of a subsequent circuit having a different reference level without introducing a dc offset or other associated amplitude distortion, or effects of capacitive coupling on low-frequency response.

7 Claims, 7 Drawing Figures

BIOLOGICAL SIGNAL SOURCE AMPLIFIER

BACKGROUND OF THE INVENTION

This invention relates to small signal amplifiers, particularly biological signal source amplifiers of the differential type that recover rapidly after presentation of an overload condition.

Input amplifiers for apparatus intended for biological signal measurement applications are usually designed for operation with very low voltages and currents. As a consequence, such input amplifiers are easily overloaded if subjected to stray signals associated with muscle action, high resistance electrode connections, stray fields, therapeutic stimulating currents of various kinds, and the like. In addition, such amplifiers are typically of the differential type whose output signal reference level may be different from the input reference level of equipment they are called upon to operate, such as, for example, a strip chart recorder, thereby creating a problem of transmitting the amplifier output signal to a subsequent circuit without a dc offset.

As an example, in a cardiac monitoring and electrical pacing apparatus for use with persons suspected of suffering from life-threatening cardiac arrhythmia, the input circuit for detecting the very small signals associated with cardiac electrical activity (hereinafter referred to for convenience as electro-cardiac signals) also receive much larger level signals associated with non-cardiac muscular activity, which often occurs as a consequence of pacing or defibrillation. Moreover, the input circuit is typically connected to the same patient electrodes as are the electrical pacing or defibrillation pulse generators. Under such circumstances the amplifier can be overloaded for a substantial period (corresponding to several beats at the normal heart rate) during and following muscular activity, particularly that caused by the application of a pacing or defibrillating pulse, at a time when it is of critical importance to know whether or not the stimulating pulse has performed its function. At such times, even a few seconds waiting for the input amplifier to recover from overload conditions can delay accurate diagnosis and thus affect the health of the patient. Further, the output of the amplifier, which may be of the differential input type having an output referenced to a voltage level other than power supply ground, should be transmitted to the subsequent circuitry without the introduction of a dc offset or other level distortion in order to ensure that the full dynamic range of that subsequent circuitry may be utilized and that the transmitted signal is as faithful to the output signal as possible.

Other methods have been previously utilized to solve the problem of overloading a biological signal source amplifier, particularly in response to the application of a therapeutic stimulating pulse. For example, Diack et al., U.S. Pat. Re. No. 30,750, describes the use of diodes placed across the amplifier input to clip the input signal to a maximum level and the use of an amplifier that can be gated off during the application of a pacing pulse. However, the voltage across a forward-biased diode is at least an order of magnitude higher than the amplitude of the electro-cardiac signals to be measured, and gating off the amplifier may not entirely prevent high level signals from overloading subsequent circuits.

Another approach facilitating recovery from overload has been described in Lewyn et al., U.S. Pat. No. 4,114,627, wherein the input circuit is automatically disconnected from the input amplifier during the application of a therapeutic pulse, and for a period of time after the pulse has occurred the input circuit is clamped through a resistor to signal ground. However, this approach will not respond to unpredictable signals such as those resulting from muscular activity, and is limited in its ability to expedite recovery by the passive clamping to ground.

Other technical references that may be of general interest with respect to the invention described and claimed herein are: Gobeli U.S. Pat. No. 3,656,487; Welborn, et al. U.S. Pat. No. 3,716,059; Gobeli, et al. U.S. Pat. No. 3,927,677; Brownlee, et al. U.S. Pat. No. 3,949,759; Wickham U.S. Pat. No. 3,972,334; Rockland, et al. U.S. Pat. No. 3,088,140; Langer, et al. U.S. Pat. No. 4,184,493; Langer, et al. U.S. Pat. No. 4,202,340; and Nordling U.S. Pat. No. 4,261,365.

Therefore, it can be seen that there is a need for a better means of facilitating recovery of a biological signal source amplifier from an input overload, and for a means for accurately translating the output of such an amplifier to a different signal level.

SUMMARY OF THE INVENTION

The present invention meets the aforementioned needs of biological signal source amplifiers and overcomes the drawbacks of the prior art by providing a novel input amplifier circuit that responds to the input signal level and actively attempts to maintain the maximum perceived signal level within an acceptable and predefined dynamic range, and by a related novel level translation circuit that permits the output of the amplifier to be transmitted to a subsequent circuit or apparatus without the introduction of any dc offset due to differing reference potentials.

The amplifier facilitates recovery from overload by "speeding up" the discharging of its reactively coupled input circuit when it is presented with an overload situation due to having been exposed to excessively large input signals, thereby preventing excessively large signals from actually overloading subsequent circuits. Since the time constant of any circuit is related to the reactance and the resistance associated with the circuit, and specifically to the time it takes to discharge the reactance elements through the resistance, applicant's invention operates by reducing the effective resistance through which the reactance must discharge and by increasing the voltage potential available to discharge the reactance, thus reducing the time constant.

In addition, by means of a switching circuit, these signals are translated without distortion from one voltage reference level to another to operate subsequent circuitry or associated equipment. This is accomplished by periodically storing temporarily the instantaneous amplitude of the signal at the output of the amplifier, referenced to one level, and transferring the stored signal to another circuit, referenced to a different level, using a simple electronic counterpart to a double-pole, double-throw switch.

It is therefore a principal object of the present invention to provide a new and improved biological signal source amplifier.

It is another object of the invention to provide in such an amplifier a method and apparatus for facilitating recovery from an input signal of excessive amplitude.

It is yet another object to provide such a method and apparatus that responds to the presentation of an excessively large input signal by actively reducing the response time constant of the amplifier input.

It is a further object of the invention to provide in such an amplifier a method and apparatus for translating a signal from one reference level to another.

The foregoing and other objectives, features and advantages of the present invention will be more readily understood upon consideration of the following detailed description of the invention taken in conjunction with the accompanying drawings.

DESCRIPTION OF A PREFERRED EMBODIMENT OF THE INVENTION

Figure 1:
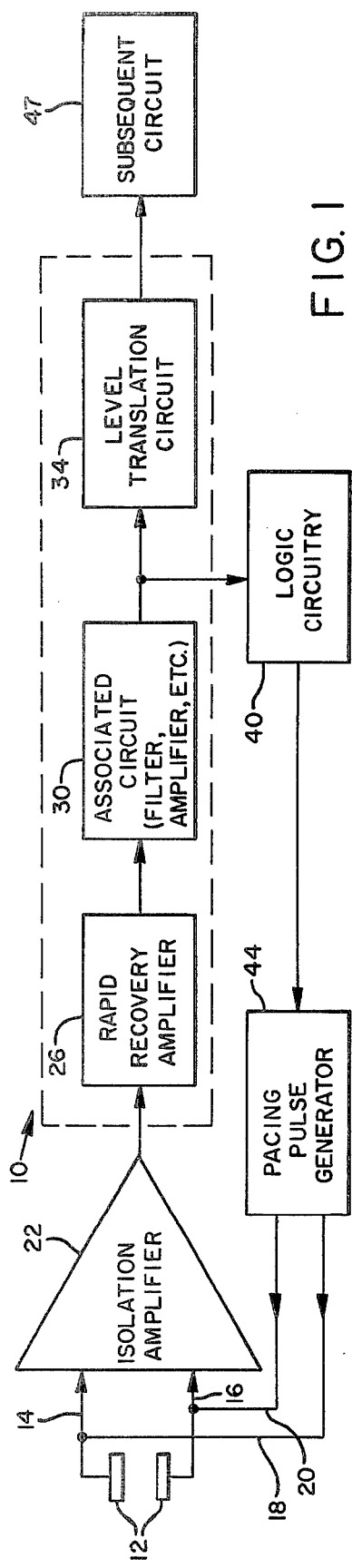
FIG. 1 is a simplified block diagram of the preferred embodiment of the present invention included in a cardiac monitoring and resuscitation apparatus.

Referring to FIG. 1, the preferred embodiment of the biological signal source amplifier 10 of the invention is shown as part of a cardiac monitoring and resuscitation apparatus which, as is commonly known in the art, combines an electro-cardiac signal detector, logic circuitry and a stimulation current generator. An apparatus of that type is shown, for example, in Diack et al., U.S. Pat. Re. No. 30,750. In such an application, the electrodes 12 are placed on the patient in any well-known manner and connected to the equipment through appropriate leads 14 and 16, respectively. To these same electrodes are also connected leads 18 and 20 from a current pulse generator 44. It is to be understood that 44 could represent a pacing pulse generator, a defibrillating pulse generator, or any other therapeutic electrical pulse generator, or any combination of them.

The leads 14 and 16 introduce the electro-cardiac signal into an isolation amplifier 22, which isolates the patient from possibly harmful or fatal leakage currents that could be present as the result of some problem in the basic equipment, such as component failure. Isolation amplifiers are well known in the art and will not be dealt with further here. The signal is then introduced into those portions of the block diagram inside the dotted outline 10. The output of the isolation amplifier 22 is input to the rapid recovery input amplifier 26, the output of which is input to associated amplifier circuitry, such as an active Butterworth filter 30, which thereafter introduces an amplified and processed electro-cardiac signal to a signal level translation circuit 34.

In the illustrative environment the output signal of the associated circuit 30 is also introduced to a logic circuit 40, where the signal may be automatically analyzed and, depending upon the result of the analysis, used to initiate an enabling signal transmitted to a pulse generator 44 which, upon receipt of such an enabling signal, generates a stimulating pulse and sends it via the conductors 18 and 20 to the electrodes 12 for application to the patient.

Figure 2:
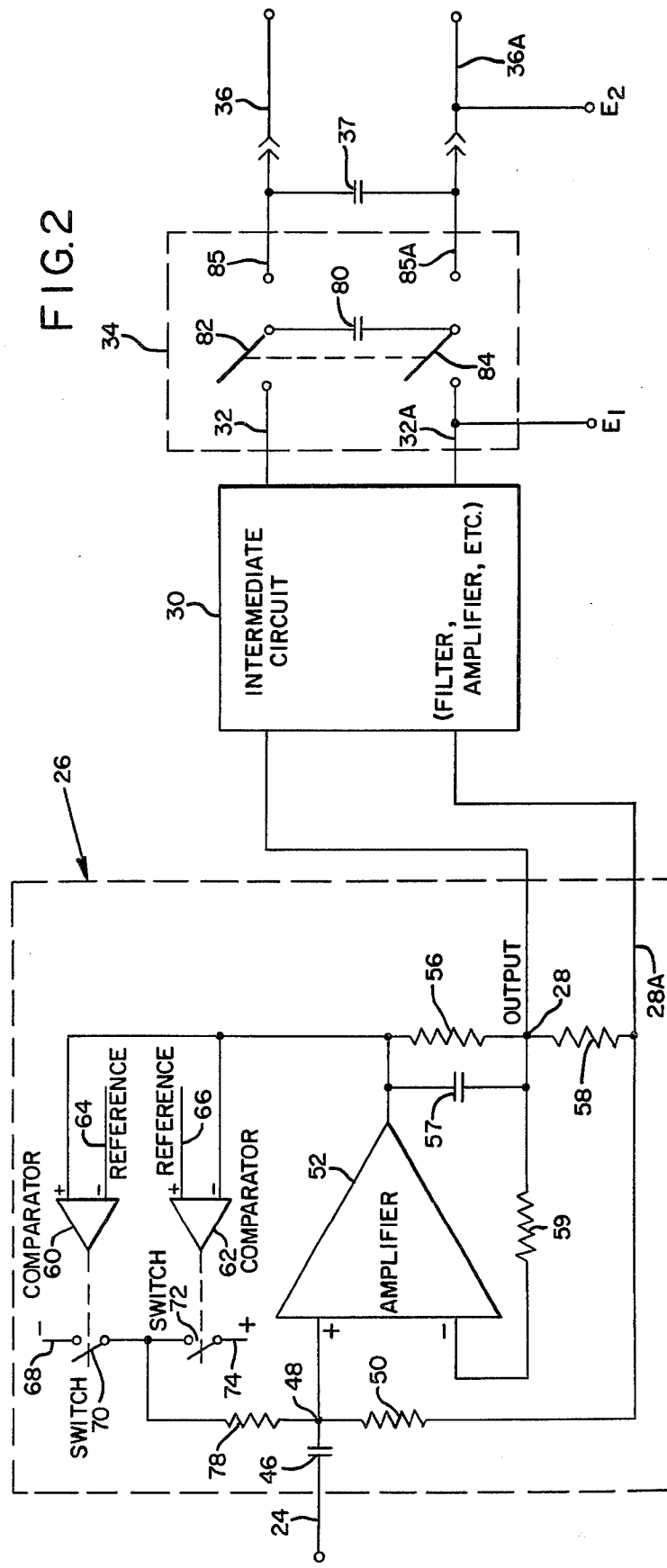
FIG. 2 is a more detailed diagram of a preferred embodiment of the invention.
Figure 3C:
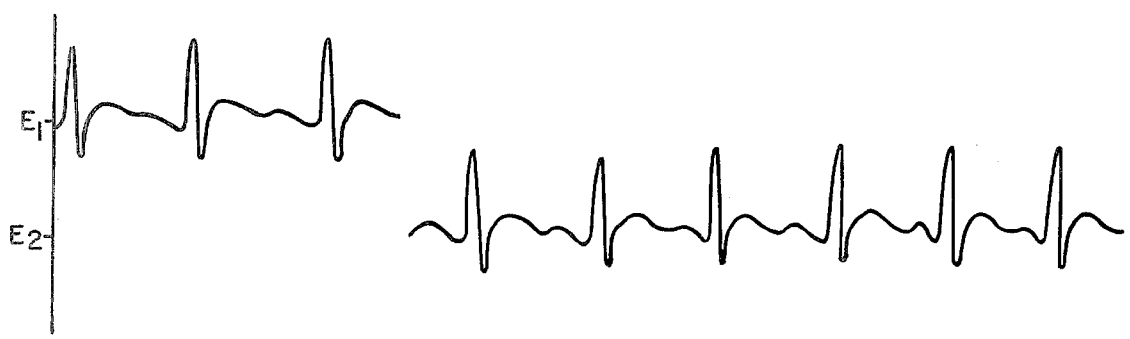
FIGS. 3A-C are a set of waveforms illustrating the operation of the invention.
Figure 3A:
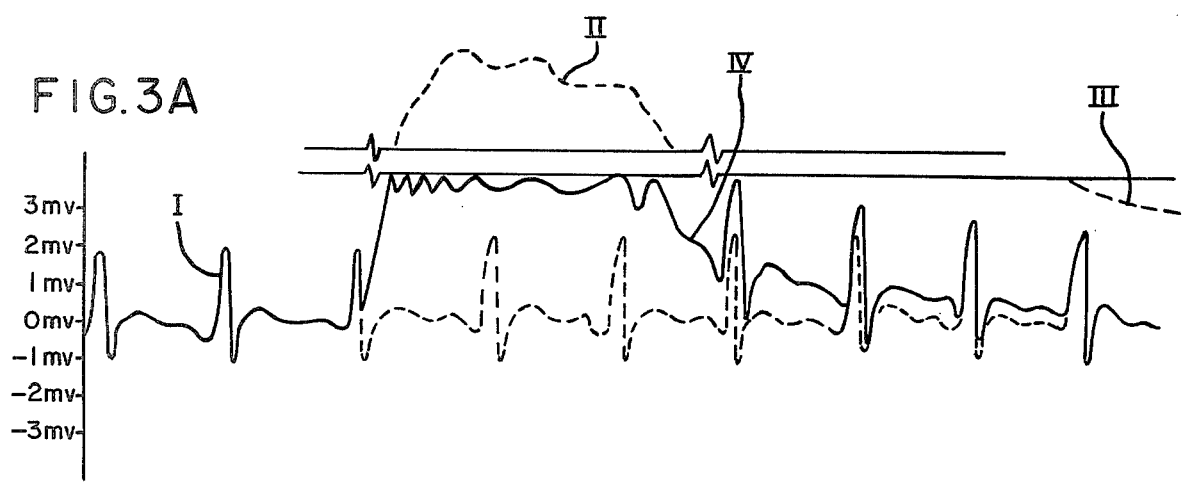
Figure 3B:
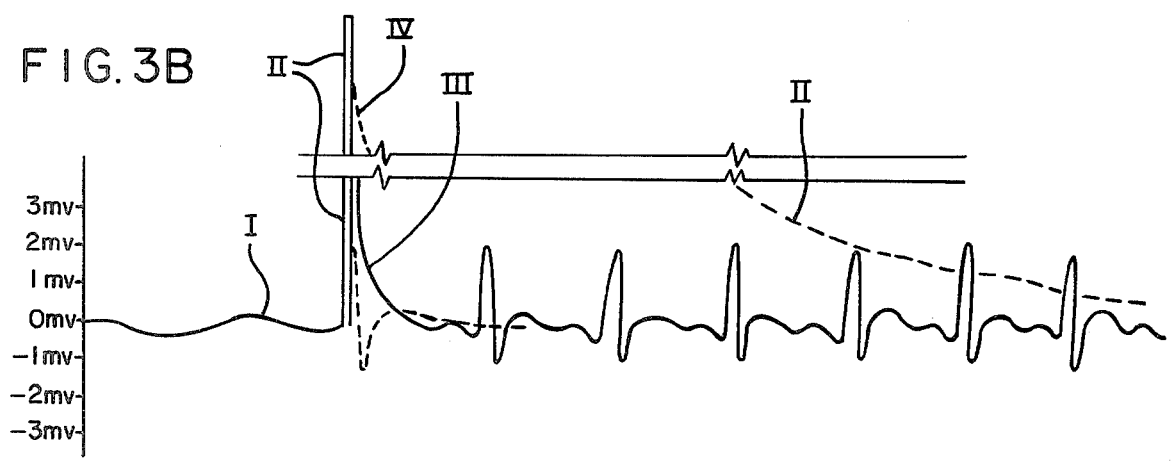

Turning now to FIG. 2, in conjunction with FIGS. 3A-C, a more detailed block diagram incorporating operative components of the invention is shown. Part I of the waveform shown in FIG. 3A, which corresponds to a signal obtained from leads 14 and 16 and which would appear at the input to the amplifier 26, represents an electro-cardiac signal for a normal heartbeat whose approximate amplitude swings are typically about +2 mv and −1 mv. Part II of the waveform represents an excessively large signal presented to the amplifier due, for example, to muscular activity. Part III represents the exponential voltage decay following the cessation of the excessively large signal in the absence of the invention, and Part IV represents the signal perceived by the amplifier of the present invention.

The electro-cardiac signal is introduced to the amplifier 26 at input 24, where it encounters an input circuit consisting of capacitor 46 and resistor 50 connected at node 48. Also connected to node 48 is the input to a differential amplifier 52 and a resistor 78. The output of the amplifier 52 is conveyed to the inputs of comparators 60 and 62, where it is compared to respective upper and lower voltage references, 64 and 66, respectively. The one end of resistor 56 is connected to the output of differential amplifier 52 and the other end of resistor 56 is connected at node 28 to the resistor 58, and through resistor 59 and to the inverting input of the operational amplifier 52, the node 28 being the output of the amplifier 26. The outputs of the comparators 60 and 62 are connected to and control switches 70 and 72 (actually MOSFET devices), respectively.

As will be recognized, the input circuit composed of resistor 50 and capacitor 46 compose a reactive coupling circuit with a definite response time determined by the time it takes capacitor 46 to charge or discharge through resistor 50. The values of 50 and 46 are chosen so that the ordinary electro-cardiac signals are transmitted therethrough without significant distortion. However, when an excessively large signal is received, such as that associated with muscular activity as shown in FIG. 3A, Part II, it will tend to drive the node 48 far beyond the level where it can discharge within the period before the next normal heartbeat occurs. Since the time constants for associated low-frequency amplifier and filtering circuits of the type utilized in cardiac monitoring, represented by the intermediate circuit 30, are long, they would also require a long time to recover. Consequently, the time of several normal heartbeats may elapse before it becomes apparent that the heart is not functioning normally and that another pacing pulse is needed.

The aforedescribed circuit of the invention reduces the loss of significant portions of the electro-cardiac signal. Ordinarily, the waveform of the regular electro-cardiac signal, when introduced into the amplifier 52, never exceeds the voltages which would be sufficient to cause the comparators 60 or 62 to operate, and will be passed through the intermediate circuit 30 to the output circuit of the invention, that is, the signal level translation circuit 34, and thereafter to whatever operational circuits follow.

On the other hand, if the waveform fed to the input circuit is excessively large the output of the amplifier 52 will drive its input to the comparators 60 and 62 either high or low, depending upon whether the input waveform is positive or negative, respectively. Comparator 60 is set to activate switch 70 when the voltage at the comparator input is greater than reference voltage 64, in response to a positive signal at point 48, thereby connecting the source of negative current 68 through the resistor 78 to the point 48, reducing the discharge time of capacitor 46, and quickly bringing the input of the amplifier to within a predetermined positive dynamic limit. Similarly, comparator 62 activates switch 72 when the voltage at the comparator input is less than reference voltage 66, in response to a negative signal at point 48, thereby connecting the source of positive current 74 through resistor 78 to the point 48, reducing the input capacitor discharge time and rapidly bringing the amplifier input to within a predetermined negative dynamic limit. Resistor 78 would typically be an order of magnitude less than resistor 50. In order to minimize the effect of changes in the input offset voltages of the comparators 60 and 62 due to changes in temperature, resistors 56 and 58 produce an output at node 28 having an effective gain with respect to the amplifier input significantly less than the gain at the output of the differential amplifier 52; preferably this effective gain is in fact unity, the differential amplifier closed loop gain being on the order of several hundred. Once the input level to the operational amplifier is brought within the prescribed limits, the comparators 26 or 28 turn off the switches 36 or 40 until the signal again exceeds the input limits.

Capacitor 57 serves to reduce the closed loop gain of amplifier 52 for noise inputs, for example signals of power line frequency and harmonics thereof, lying above the usual spectrum of interest of biological signals. By this means, the dynamic limits of the amplifier 26 are increased for out-of-band signals, thus preventing the loss of possibly smaller biological signals through inappropriate activation of the rapid recovery mechanism. Typically such smaller biological signals are recoverable due to low- or band-pass filtering contained in the intermediate circuit 30 despite the presence of noise at input 24.

Since the circuit operates during the time the actual input level exceeds the dynamic limits of the amplifier, the perceived level will be maintained generally within those limits and the circuit will be ready to accept normal electro-cardiac signals shortly after the cessation of the excessive input level. When an especially excessive input signal is encountered, the circuit may not be able to pull the perceived level within the dynamic limits so rapidly, but will nevertheless facilitate rapid recovery from an overload.

As the amplified signal is sent to other parts of the instrument for further processing, it may be called upon to operate equipment whose input voltage reference level is different from the level to which the output of the above described amplifier is referenced. For example, in the specific circuit of the preferred embodiment, shown in FIG. 4, differential operational amplifiers are utilized wherein, due to the use of only a positive supply voltage, the output signal is referenced to a signal ground that is offset from the power supply ground by +4 volts. If, as is typically the case, the input of the other equipment is referenced to power supply ground, a problem exists of transmitting the amplified signal to the other equipment without introducing a dc offset and other accompanying distortion, or the effects of capacitive coupling on low frequency response. The circuit of the invention accomplishes this function by translating the output signal from its reference level to another reference level.

Turning again to FIG. 2, the output signal of amplifier 26 passes through the intermediate circuitry 30 and appears between the output signal connection 32 and the output reference connection 32A, having a potential $E_1$ to which it is referenced. The signal translation circuit 34 includes a capacitor 80, acting as a signal storage means, having a signal storage connection 82 and a storage reference connection 84. (The dotted line between the two connections indicates that the two connections are switched at the same time.) The subsequent circuit 47 has input connection 36 and input reference connection 36A which may be at a different potential $E_2$ with reference to the output of amplifier 26.

The storage capacitor 80 is first connected across the output of the amplifier 26 by terminals 32 and 32A. The voltage across the capacitor will charge to the potential existing at that instant across the amplifier output connections. Following such charging action, the connections 82 and 84 of the storage capacitor are switched to the connections 85 and 85A, where charge stored on the capacitor is transferred in part to a terminating capacitor 87 until the voltages across the two capacitors are equal. The voltage across capacitor 87 is applied to the input connections 36 and 36A of the subsequent circuit. The switching rate of the capacitor is made sufficiently high with respect to the frequency components of the output signal, for example 18 kHz in the illustrative application, that little charge is lost during the transition and the output waveform is translated without appreciable distortion. Consequently, as shown by FIG. 3C, what appears on the input connections 36 and 36A is a waveform representative of the output of the amplifier (having switching frequency components that may be removed by subsequent circuits as is commonly known in the art), but referenced to the dc level required to operate the subsequent circuit 47.

Figure 4:
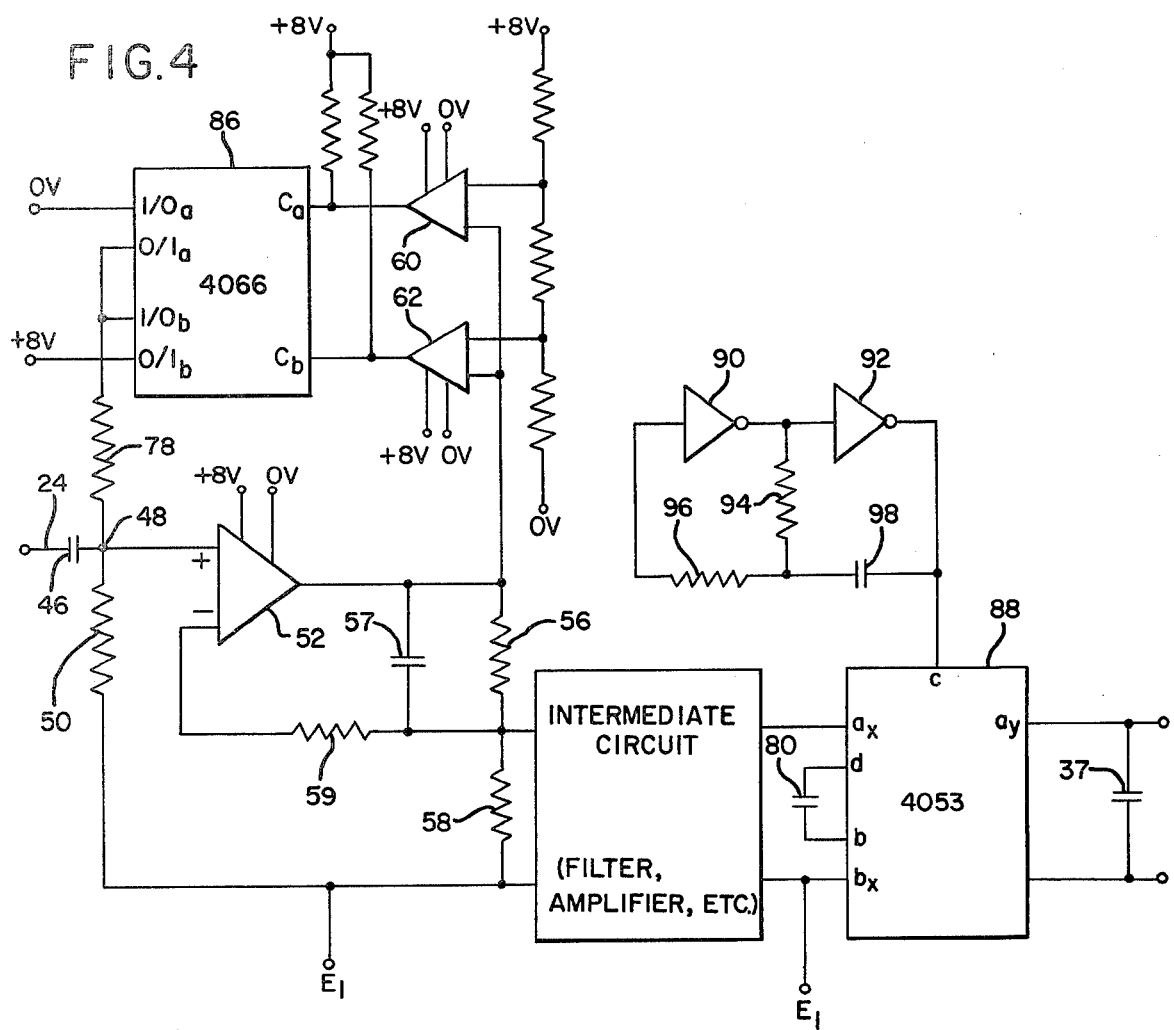
FIG. 4 is a schematic diagram of circuits implementing the preferred embodiment of the invention.

FIG. 4 shows a specific circuit for implementation of the preferred embodiment. In that circuit device 86 performs the functions of switches 70 and 72 and is a 4066 bilateral analog switch. Device 88 performs the functions of switching the connectors 82 and 84 and is a 4053 analog multiplexer, inverters 90 and 92, resistors 94 and 96, and capacitor 98 forming an oscillator for driving the analog multiplexer. However, it is to be recognized that the present invention could be implemented by other circuit configurations using different components without departing from the principles of the invention.

Figure 5:
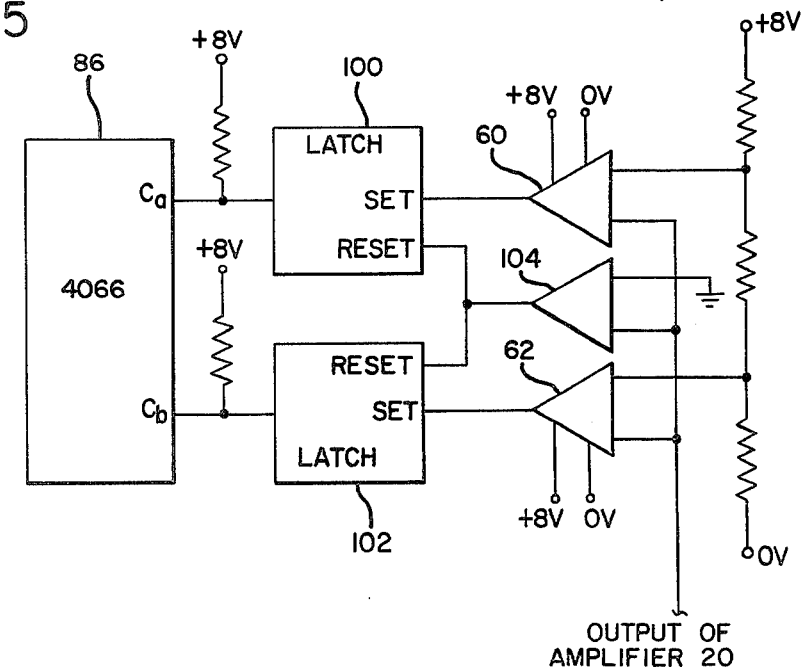
FIG. 5 is a simplified schematic diagram of an alternative embodiment of the invention.

FIG. 5 shows a simplified schematic diagram of an alternative embodiment of the rapid recovery amplifier portion of the invention. In this embodiment latches 100 and 102 are interposed between the comparators 60 and 62, respectively, and the analog switch 86, and a third comparator 104 is added to compare the output of the amplifier 20 to signal ground. The effect of this is to turn on the appropriate latch when the input signal exceeds the dynamic limits but not to reset the latches until the input returns to the reference level, thereby increasing the time period during which the rapid recovery mechanism is activated.

This alternative embodiment more rapidly reduces distortion in the waveform that follows the occurrence of an excessive input signal and is advantageous where the input signal may be especially excessive, as where a cardiac monitoring device is left electrically connected to the patient during the application of a pacing or defibrillation pulse. An example of its effect under such circumstances is illustrated by FIG. 3B, wherein Part I represents an electro-cardiac signal during cardiac arrest, Part II represents the waveform resulting from the application of a defibrillation pulse, and Part III represents the waveform returning to the signal ground reference level as a result of the action of the invention. Part IV of the waveform represents the decay of the signal in the absence of the invention.

The terms and expressions which have been employed in the foregoing specification are used therein as terms of description and not of limitation, and there is no intention, in the use of such terms and expressions, of excluding equivalents of the features shown and described or portions thereof, it being recognized that the scope of the invention is defined and limited only by the claims which follow.

What is claimed is:

1. In a biological-signal-source amplifier, a signal input circuit for facilitating recovery from an input signal of excessive amplitude, said input circuit comprising:
   (a) input coupling means, having a characteristic reactance, for coupling an input signal to said amplifier;
   (b) first comparator means, responsive to said input coupling means, for comparing the amplitude of said coupled input signal to a first reference value;
   (c) second comparator means, responsive to said input coupling means, for comparing the amplitude of said coupled input signal to a second reference value;
   (d) current source means, connected to said input coupling means and responsive to said first and second comparator means, for supplying to said input coupling means additional current of one polarity when said coupled input signal exceeds said first reference value, and additional current of the opposite polarity when said coupled input signal is less than said second reference value, thereby decreasing the time required for said coupled input signal to return to a value between said first and second reference values.

2. The input circuit of claim 1, wherein said input coupling means comprises a reactive element connected to a first, input impedance element and said current source means comprises a second impedance element connected to said reactive element and said first impedance element at the connection thereof, said second impedance element being connected to a current source of negative polarity when said coupled input signal exceeds said first reference value and to a current source of positive polarity when said coupled input signal is less than said second reference value.

3. The input circuit of claim 2, wherein said input coupling means, said first impedance element, and said second impedance element are connected at the connection thereof to the input of an amplifier element and said first and second comparator means are adopted to compare the output of said amplifier element to reference potentials proportional to said first and second reference levels, respectively.

4. The input circuit of claim 3, wherein said output of said amplifier element is connected to a circuit network that provides an effective output amplitude representing a gain with respect to the input of said amplifier element significantly less than the gain represented by said output of said amplifier element.

5. The input circuit of claim 4, wherein said network is adapted to decrease said gain represented by said output of said amplifier element for given signal components as the frequency of said signal components increases.

6. The input circuit of claim 2, wherein said first impedance element is a first resistor, and said second impedance element is a second resistor, said second resistor being connected alternatively to said first or second current sources by electronic switches controlled by said comparator means.

7. The input circuit of claim 1, further comprising third comparator means, responsive to said input coupling means, for comparing the amplitude of said coupled input signal to a third reference value, and said current source means includes means, responsive to said third comparator means, for continuing the supply of additional current to said input coupling means until said coupled input signal level crosses said third reference level.

* * * * *